(12) United States Patent
Choi et al.

(10) Patent No.: US 9,796,789 B2
(45) Date of Patent: Oct. 24, 2017

(54) BIOMEMORY DEVICE COMPRISING HETEROLAYER OF RECOMBINANT PROTEIN AND INORGANIC PARTICLE

(75) Inventors: Jeong Woo Choi, Seoul (KR); Taek Lee, Seoul (KR); Jun Hong Min, Seongnam-Si (KR)

(73) Assignee: INDUSTRY-UNIVERSITY COOPERATION FOUNDATION SOGANG UNIVERSITY, Seoul (KR)

( * ) Notice: Subject to any disclaimer, the term of this patent is extended or adjusted under 35 U.S.C. 154(b) by 957 days.

(21) Appl. No.: 13/564,136

(22) Filed: Aug. 1, 2012

(65) Prior Publication Data

US 2013/0157335 A1 Jun. 20, 2013

(30) Foreign Application Priority Data

Dec. 16, 2011 (KR) ........................ 10-2011-0136406

(51) Int. Cl.
| | |
|---|---|
| *C07K 17/14* | (2006.01) |
| *C12N 11/14* | (2006.01) |
| *G11C 13/00* | (2006.01) |
| B82Y 10/00 | (2011.01) |
| *B82Y 5/00* | (2011.01) |
| *B82Y 30/00* | (2011.01) |
| *B82Y 15/00* | (2011.01) |

(52) U.S. Cl.
CPC .............. *C07K 17/14* (2013.01); *B82Y 10/00* (2013.01); *C12N 11/14* (2013.01); *G11C 13/0019* (2013.01); *B82Y 15/00* (2013.01); *B82Y 30/00* (2013.01)

(58) Field of Classification Search
None
See application file for complete search history.

(56) References Cited

PUBLICATIONS

Lee, Taek; El-Said, Waleed Ahmed; Min, Junhong; Oh, Byung-Keun; Choi, Jeong-Woo "Verification of surfactant CHAPS effect using AFM for making biomemory device consisting of recombinant azurin monolayer" Ultramicroscopy, May 2010,110(6), pp. 712-717 (doi:10.1016/j.ultramic.2010.02.037).*

Delfino, Ines and Cannistrano, Salvatore "Optical investigation of the electron transfer protein azurin—gold nanoparticle system" Biophys. Chem., 2009 (pub. online Sep. 30, 2008), 139(1), pp. 1-7 (doi:10.1016/j.bpc.2008.09.016).*

(Continued)

*Primary Examiner* — Chris R Tate
*Assistant Examiner* — Aaron J Kosar
(74) *Attorney, Agent, or Firm* — Harness, Dickey & Pierce, P.L.C.

(57) ABSTRACT

The present invention relates to a biomemory device, comprising (a) a substrate; and (b) a heterolayer comprising a protein having a redox potential and an inorganic particle; wherein the heterolayer is immobilized on the substrate. By applying inorganic particles, the present invention provides a biomemory device capable of enhancing low current signals detected electron transfer between biomolecules and substrates up to at least five (5) times greater signals. The present invention is capable of controlling the redox states with help of redox potentials of proteins depending on applied potential. The present invention provides a new-concept biomemory device as an information storage device based on the principle of electron transfer of a naturally occurring biomolecule.

4 Claims, 4 Drawing Sheets

(56) References Cited

PUBLICATIONS

Domenici, F; Bizzarri, A.R.; Cannistraro, S "SERS-based nanobiosensing for ultrasensitive detection of the p53 tumor suppressor" International Journal of Nanomedicine, Sep. 19, 2011, 6, pp. 2033-2042. doi: 10.2147/IJN.S23845.*

Yagati, A.K.; Lee, T; Min, J; Choi, J-W "A robust nanoscale biomemory device composed of recombinant azurin on hexagonally packed Au-nano array" Biosensors and Bioelectronics, 2013 (pub. online Aug. 3, 2012), 40, pp. 283-290. doi:10.1016/j.bios.2012.07.055.*

Choi et al., "Bioelectronic Device Consisting of Cytochrome c/poly-L-aspartic Acid Adsorbed Hetero-Langmuir-Blodgett Films," J. Biotechnol. 94:225-233, 2002.

Kim et al., "Nanoscale Protein-Based Memory Device Composed of Recombinant Azurin," Biomaterials 31:1293-1298, 2010.

Lee et al., "Multilevel Biomemory Device Consisting of Recombinant Azurin/Cytochrome c," Adv. Mater. 21:1-5, 2009.

Lee et al., "Signal Enhancement of Electrochemical Biomemory Device Composed of Recombinant Azurin/Gold Nanoparticle," Electroanalysis 23:2023-2029, 2011.

\* cited by examiner

BIOMEMORY DEVICE COMPRISING HETEROLAYER OF RECOMBINANT PROTEIN AND INORGANIC PARTICLE

CROSS-REFERENCE TO RELATED APPLICATIONS

This application claims priority from Korean Patent Application No. 10-2011-0136406, filed on Dec. 16, 2011, in the Korean Intellectual Property Office, the disclosure of which is incorporated herein by reference.

BACKGROUND OF THE INVENTION

Field of the Invention

The present invention relates to a biomemory device, comprising a substrate and a heterolayer comprising a protein having a redox potential and an inorganic particle.

Description of the Related Art

Electrochemical properties of biomolecules have been widely studied to understand the behaviors, mechanisms, and fundamental concepts of living organisms such as respiration, sequential electron transfers, and photosynthesis [1]. Electron transfer has been extensively studied due to its various potential applications such as in biochips, biosensors and bioelectronics. For example, Woolley et al. monitored the electrochemical properties of anticancer compounds on cells [2]. In addition, living cells have been widely investigated under many electrochemical conditions such as electron transfer between electroactive centers in cells and electrodes [3], and electric cell substrate impedance sensing [4-6]. Furthermore, electrochemistry can be widely applied to biosensors using enzymes, antibodies, nucleic acids, peptide nucleic acids, and aptamers [7-10]. Bioelectrochemistry can also be the basis for the development of electrochemical-based bioelectronics. It is possible to detect electrochemical signals from living organisms, for example, protein, DNA, cells and other organisms [11-14].

SUMMARY OF THE INVENTION

The inventors of the present invention have made intensive studies to develop a biomemory device based on an electrochemical system controlling electron transfer of protein molecules. Especially, in applying potential state, we have made efforts to enhance signal from the device capable of exhibiting memory device functions such as "write" and "erase". As results, we have developed a novel biomemory device comprising a substrate, and a heterolayer comprising a protein having a redox potential and an inorganic particle in which the protein directly immobilized on the substrate is preferably a recombinant protein with introduced cysteine residues forming a self-assembled monolayer (SAM) and the inorganic particle is indirectly immobilized on the substrate. We have found that the novel biomemory device may effectively provide an enhanced signal.

Accordingly, it is an object of this invention to provide a biomemory device.

It is another object of this invention to provide a method for fabricating a biomemory device.

Other objects and advantages of the present invention will become apparent from the following detailed description together with the appended claims and drawings.

BRIEF DESCRIPTION OF THE DRAWINGS

FIG. 2a shows the oxidation and reduction potentials of the recombinant azurin/Au nanoparticle (5 nm) is 432.11 mV and 263.74 mV, respectively. FIG. 2b shows the oxidation and reduction potentials of the recombinant azurin/Au nanoparticle (10 nm) is 470.15 mV and 264.77 mV, respectively. FIG. 2c shows the oxidation and reduction potentials of the recombinant azurin/Au nanoparticle (20 nm) is 472.22 mV and 351.06 mV, respectively. FIG. 2d shows the oxidation and reduction potentials of the recombinant azurin/Au nanoparticle (40 nm) is 457.89 mV and 358.91 mV, respectively. FIG. 2e shows the oxidation and reduction potentials of the recombinant azurin/Au nanoparticle (60 nm) is 442.17 mV and 288.53 mV, respectively. FIG. 2f shows the reduction currents and oxidation currents of the recombinant azurin/gold nanoparticle heterolayer in various size (5 nm, 10 nm, 20 nm, 40 nm, and 60 nm).

FIG. 3a shows the surface topography of the immobilized recombinant azurin layer, which contained irregular shaped lumps that were 20-30 nm, FIG. 3b shows the adsorption of gold nanoparticle. FIG. 3c shows the comparison between the angle shift for the recombinant azurin on the Au substrate and the gold nanoparticle self-assembled on the recombinant azurin modified Au surface.

FIG. 4a shows a diagram of the applied potentials, FIG. 4b shows that the current inflow and out flow from the fabricated electrode were stable when an oxidation potential (432.11 mV) and reduction potential (236.74 mV) were applied repeatedly.

DETAILED DESCRIPTION OF THIS INVENTION

Figure 1:
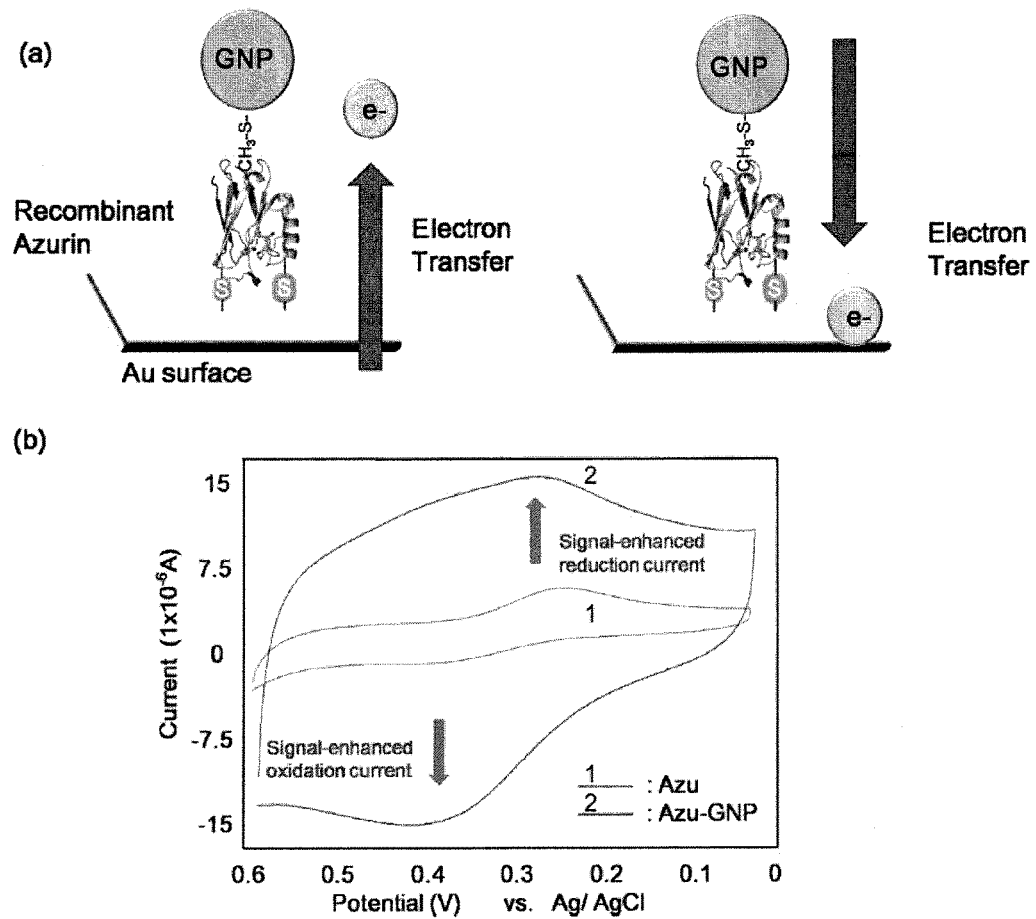
FIG. 1a shows a schematic of the electron transfer between the recombinant azurin and the Au (gold) nanoparticle.
FIG. 1b shows the cyclic voltammetry of the recombinant azurin (Curve 1) and recombinant azurin/gold nanoparticle (Curve 2).

In one aspect of this invention, there is provided a biomemory device comprising (a) a substrate, and (b) a heterolayer comprising a protein having a redox potential and an inorganic particle; wherein the heterolayer is immobilized on the substrate.

The inventors of the present invention have made intensive studies to develop a biomemory device based on an electrochemical system controlling electron transfer of protein molecules. Especially, in applying potential state, we have made efforts to enhance signal from the device capable of exhibiting memory device functions such as "write" and "erase". As results, we have developed a novel biomemory device comprising a substrate, and a heterolayer comprising a protein having a redox potential and an inorganic particle in which the protein directly immobilized on the substrate is preferably a recombinant protein with introduced cysteine residues forming a self-assembled monolayer (SAM) and the inorganic particle is indirectly immobilized on the substrate. We have found that the novel biomemory device may effectively provide an enhanced signal.

According to a preferable embodiment of the present invention, the protein is a recombinant protein having a redox potential and has a cysteine residue introduced at its N- or C-terminal. The recombinant protein is directly immobilized on the substrate via the thiol group of the cysteine residue.

Another feature of the present invention is that a protein biomolecule having a redox potential is used as a memory device and a cysteine residue is introduced at the N- or C-terminal of the protein to form a stable self-assembled monolayer (SAM) on a substrate. The introduced cysteine residue forms a stable monolayer with good orientation by means of its thiol group on a substrate, specifically on a metal substrate, more specifically on a gold (Au) substrate.

According to a preferable embodiment, the recombinant protein has 2-10 cysteine residues. If the number of the introduced cysteine residues is less than 2, i.e. one, the function of the cysteine residue as an anchoring site decreases greatly. And, if the number of the cysteine residues exceeds 10, disulfide bonds formed between the introduced cysteine residues make purification of the recombinant protein difficult and greatly decrease the function of the cysteine residues as an anchoring site.

According to another preferable embodiment, the recombinant protein has 2-3 cysteine residues, most specifically 2 cysteine residues.

The protein is directly immobilized via the thiol group of the introduced cysteine. As used herein, the term "direct immobilization" refers to immobilization of a protein molecule directly on a substrate without help from another linker.

The direct immobilization is advantageous in that unnecessary resistance layers can be decreased in electron transfer process and immobilization capacity can be maximized under given conditions.

A linker is most commonly used at present as a technique to immobilize a protein on a substrate. However, this method has disadvantages of (i) requiring much excessive processes, (ii) exhibiting low immobilization rate and (iii) generating the insulating effect of linker layers.

The direct immobilization may overcome the defects of the existing techniques.

The recombinant protein used as the memory device in the present invention may be any protein having a redox potential and capable of accepting or releasing an electron. For example, the recombinant protein suitable to the present invention includes, but is not limited to, a metalloprotein containing a metal ion, such as flavodoxin, plastocyanin, thioredoxin, etc.

According to a preferable embodiment, the recombinant protein having a redox potential is a metalloprotein containing a metal ion, more preferably azurin, hemoglobin, myoglobin, hemerythrin, cytochrome, iron-sulfur protein, rubredoxin, plastocyanin, ferritin, ceruloplasmin, carbonic anhydrase, vitamin $B_{12}$-dependent enzyme, nitrogenase, superoxide dismutase, chlorophyll-containing protein, calmodulin, glucose 6-phosphatase, hexokinase, DNA polymerase, vanabin, arginase, catalase, hydrogenase, iron-responsive element-binding protein, aconitase, urease, cytochrome oxidase, laccase, alcohol dehydrogenase, carboxypeptidase, aminopeptidase, β-amyloid, nitrate reductase, glutathione peroxidase, metallothionein or phosphatase, much more preferably azurin, cytochrome a, cytochrome b or cytochrome c, most preferably azurin.

One of the striking features of the present invention is that the inorganic particle is covalently immobilized to the protein having redox potential immobilized on the substrate, so that the inorganic particle is allowed to be indirectly immobilized on the substrate. Therefore, the biomemory device in which a heterolayer comprising a protein having the redox potential and inorganic particle immobilized on a substrate is completed.

Preferably, the inorganic particle is a metal particle, metal oxide particle, alloy particle or semiconductor particle.

When the inorganic particle is a metal particle, the inorganic particle includes preferably Group 1 elements, Group 2 elements, transition metal elements, Group 12 elements, Group 13 elements, lanthanoids or actinides, more preferably, Ba, Cr, Co, Mn, Fe, Ni, Cu, Zn, Nb, Pd, Ag, Pt, Au, Tb, Gd, Dy, Ho, Er, Sm, Nd and its multi element heterocomplex, but not limited to.

When the inorganic particle is a metal oxide particle, the inorganic particle includes preferably, $M_xO_y$(M represents transition elements selected from Ba, Cr, Mn, Fe, Co, Ni, Cu, Zn, Nb, Pd, Ag, Pt, and Au, or any lathanoids or actinides selected from Gd, Tb, Dy, Ho, Er, Sm, and Nd, $0<x\leq16$, $0<y\leq8$), or $M^a_xM^b_yM^c_z$($M^a$ represents at least one metal element selected from Group 1 metal elements, Group 2 metal elements, Group 13 metal elements, Group 14 metal elements, Group 15 metal elements, Group 16 elements, transition metal element, lanthanoids, and actinides, $M^b$ represents at least one metal element selected from transition metal element selected from Ba, Cr, Mn, Fe, Co, Ni, Cu, Zn, Nb, Pd, Ag, Pt, and Au, or lanthanoides or actinides selected from Gd, Tb, Dy, Ho, Er, Sm, and Nd, $0\leq x\leq16$, $0<y\leq16$, $0<z\leq8$) and its multi elements heterocomplex, but not limited to.

When the inorganic particle is a alloy particle, the inorganic particle includes preferably, $M_xM'_y$($M_x$ represents at least one metal element selected from the transition element selected from Ba, Cr, Mn, Fe, Co, Ni, Cu, Zn, Nb, Pd, Ag, Pt, and Au, and lathanoids or actinides selected from Gd, Tb, Dy, Ho, Er, Sm, and Nd, $M'_y$ represents at least one metal element selected from Group 1 elements, Group 2 elements, Group 13 elements, Group 14 elements, Group 15 elements, Group 16, transition metal element, lanthanoids, and actinides, $0<x\leq20$, $0\leq y\leq20$) and its multi elements heterocomplex, but not limited to.

When the inorganic particle is a semiconductor particle, the inorganic particle includes preferably, the semiconductor particle includes $M_aM'_b$($M_a$ or $M'_b$ represents at least one metal element selected from Group 13 elements, Group 12 elements, Group 14 elements, Group 15 elements, Group 16 elements, $0<a\leq20$, $0<b\leq20$) and its multi elements heterocomplex as, but not limited to.

According to a preferable embodiment of the present invention, the inorganic particle is a metal particle, more preferably an Au (gold) particle.

Preferably, the Au particle is 1-100 nm in size, more preferably 1-50 nm, most preferably 1-10 nm.

The heterolayer comprising the protein having the redox potential and the inorganic particle is immobilized on a substrate via the protein. Preferably, the inorganic particle is covalently bonded to the protein and indirectly immobilized on the substrate via the protein.

The substrate used in the biomemory device of the present invention may be any one used in the fabrication of memory devices. In an exemplary embodiment of the present invention, the substrate is a metal, metal oxide, glass, ceramic, quartz, silicon, semiconductor, Si/$SiO_2$ wafer, germanium, gallium arsenide, carbon, carbon nanotube, polymer, sepharose or agarose substrate, more specifically a metal substrate, most specifically a gold (Au) substrate.

As used herein, the term "gold substrate" refers to a substrate having a surface coated with gold.

The immobilization of the cysteine-modified protein and the inorganic particle onto the substrate may be carried out as follows:

First, a substrate, preferably a gold substrate, is annealed at high temperature and cleaned with piranha solution. Then, the protein is dispersed on the surface of the gold substrate and allowed to stand so that a SAM is formed on the substrate. The substrate immobilized with the protein is immersed in 1-octadecathiol solution and dipped the substrate into a solution comprising the inorganic particle to combine the inorganic particle with the protein.

Preferably, the biomemory device of the present invention is operated by applying a reduction potential and an oxidation potential.

One of the features of the present invention is that the cysteine-modified protein molecule is self-assembled on the substrate, specifically the gold substrate, through the thiol group of the cysteine residue, covalently bonded with the inorganic particle to the protein molecule and is utilized as a nano-scale information storage device using the intrinsic electron transfer properties of the protein dependent on the applied voltage.

For the protein-based biomemory device of the present invention to be operated electrically, the memory device of the present invention may be a reversibly changeable and electrically readable electronic device comprising the followings. The electronic device comprises a substrate. The substrate is the same as described above and its surface is electrically coated with gold as described in the following examples. A redox active layer is formed on the substrate. The SAM of the cysteine-modified recombinant protein having a redox potential is used as the redox active layer in the present invention. The redox active layer is placed under specific electronic conditions, e.g. oxidation state or reduction state, by the recombinant protein. An electrode is connected to the redox active layer. The device of the present invention comprises an electric field source, e.g. a voltage supply unit, linked to the substrate, the electrode, or both. Flow of electrons is induced by a voltage or an electric beam supplied to the electric field source, thus enabling the memory function.

Thus, when the memory device of the present invention is constructed electrochemically, the device of the present invention comprises: (i) the substrate, (ii) the SAM as the redox active layer which is immobilized on the substrate and contains the cysteine residues introduced to the recombinant protein having a redox potential, (iii) the electrode linked to the redox active layer and (iv) the electric field source supplying the voltage or electric beam to the substrate and/or the electrode.

Hereunder is given a specific example the biomemory device of the present invention is constructed electrochemically.

The present invention relates to an information storage device enabling to change the oxidation and reduction state of proteins immobilized by adjusting applied voltage according to an electrochemical method. The substrate having the protein layer is incubated in an electrolyte solution, e.g. a HEPES electrolyte. The substrate is operated by connecting to a potentiostat as a working electrode, and a reference electrode (e.g., Ag/AgCl) and a counter electrode (e.g., Pt) are incorporated into the electrolyte. The reference electrode is a reference to read the potential changes of the working electrode in the potentiostat during voltage sweep. The counter electrode is a passage of electrons flowing as a result of the control of potential by the potentiostat. Such a three-electrode system is one of the most commonly used systems in the field of electrochemistry. In the simple electrochemical system described above, a voltage-current curve is obtained using the cyclic voltammetry method. An open-circuit potential is measured to investigate the equilibrium potential of the electrochemical system constructed. The open-circuit potential refers to a potential difference formed due to the intrinsic property of the protein layer and the electrolyte in a voltage-free state, i.e. in a circuit-broken state, naturally reaching equilibrium in the constructed system. Based on the above principle, a system can be artificially made close to the equilibrium state by applying an open-circuit potential to the system if the open-circuit potential is known. To describe in more detail, after the protein is reduced by accepting electrons from the electrolyte as the reduction potential is applied to the protein layer, electrons are released while the protein returns to the equilibrium state as the open-circuit potential is applied. Conversely, after the protein is oxidized by releasing the electrons, it returns to the original potential state by accepting electrons when the open-circuit potential is applied. Therefore, the open-circuit potential allows to read the redox state of the protein layer.

According to a preferable embodiment, the biomemory device of the present invention comprising the azurin protein and gold nanoparticles immobilized on substrates shows a redox current at least five (5) times greater than those of conventional devices comprising a monolayer of the azurin protein immobilized on substrates (FIG. 1b).

In another aspect of this invention, there is provided a method for fabricating a biomemory device comprising a heterolayer immobilized on a substrate comprising a protein having a redox potential and an inorganic particle, comprising:

(a) immobilizing the protein having a redox potential directly to the substrate; and (b) immobilizing the inorganic particle to the protein through a covalent bond.

According to a preferred embodiment, the protein having a redox potential is a recombinant protein and is directly immobilized on the substrate via a cysteine residue introduced to the recombinant protein.

According to a preferred embodiment, the protein is a metalloprotein, more preferably azurin, hemoglobin, myoglobin, hemerythrin, cytochrome, iron-sulfur protein, rubredoxin, plastocyanin, ferritin, ceruloplasmin, carbonic anhydrase, vitamin $B_{12}$-dependent enzyme, nitrogenase, superoxide dismutase, chlorophyll-containing protein, calmodulin, glucose 6-phosphatase, hexokinase, DNA polymerase, vanabin, arginase, catalase, hydrogenase, iron-responsive element-binding protein, aconitase, urease, cytochrome oxidase, laccase, alcohol dehydrogenase, carboxypeptidase, aminopeptidase, β-amyloid, nitrate reductase, glutathione peroxidase, metallothionein or phosphatase, most preferably azurin.

According to a preferred embodiment, the inorganic particle is a metal particle, a metal oxide particle, an alloy particle or a semiconductor particle, more preferably a metal particle, most preferably a gold (Au) particle.

According to a preferred embodiment, the gold (Au) particle is 1-100 nm in size.

According to a preferred embodiment, the heterolayer is immobilized on the substrate via the protein.

According to a preferred embodiment, the inorganic particle is covalently bonded to the protein and is indirectly immobilized on the substrate via the protein.

According to a preferred embodiment, the substrate is a metal, metal oxide, glass, ceramic, quartz, silicon, semiconductor, $Si/SiO_2$ wafer, germanium, gallium arsenide, carbon, carbon nanotube, polymer, sepharose or agarose substrate, more preferably a gold (Au) substrate.

According to a preferred embodiment, the biomemory device is operated by applying a reduction potential and an oxidation potential.

The features and advantages of the present invention will be summarized as follows:

(a) The present invention provides a biomemory device in which a protein having a redox potential and an inorganic particle are directly immobilized on a substrate.

(b) By applying inorganic particles, the present invention provides a biomemory device capable of enhancing low current signals detected electron transfer between biomolecules and substrates up to at least five (5) times greater signals.

(c) The present invention is capable of controlling the redox states with help of redox potentials of proteins depending on applied potential.

(d) The present invention provides a new-concept biomemory device as an information storage device based on the principle of electron transfer of a naturally occurring biomolecule.

The present invention will now be described in further detail by examples. It would be obvious to those skilled in the art that these examples are intended to be more concretely illustrative and the scope of the present invention as set forth in the appended claims is not limited to or by the examples.

EXAMPLES

1. Materials and Methods

Experimental Materials

Au substrates (Au (50 nm)/Cr (2 nm)/$SiO_2$ wafers) were purchased from G-mek (Korea) and used in the electrochemical experiments and AFM analysis. The Pt Counter electrode and Ag/AgCl reference electrode were purchased from BAS (USA). The recombinant azurin was expressed and purified from E. coli DE3 [25]. The gold nanoparticle was purchased from BBI international (UK). 1-Octadecanethiol ($CH_3(CH_2)_{17}SH$: ODT), was purchased from Sigma Aldrich Co (USA). HEPES (4-(2-hydroxyethyl)-1-piperazineethanesulfonic acid) solution was used as the electrolyte buffer and was purchased from Sigma Aldrich Co (USA). Distilled and deionized (DI) water was used to clean the substrates.

Genetic Engineering of Pseudomonas aeruginosa Azurin

An Escherichia coli strain DH5α was used as the host for subcloning. Standard techniques were employed throughout this work. The gene encoding blue copper protein azurin was amplified using polymerase chain reaction (PCR) from the genomic DNA of Pseudomonas aeruginosa. The forward primer was designed to contain a NcoI restriction enzyme site and the reverse primer was designed to contain a BamHI restriction enzyme site The PCR product was purified using a DNA purification kit (QIAZEN, USA) and digested with two restriction enzymes for NcoI and BamHI (New England Biolabs, UK). The digested DNA fragments were ligated with a pET-21a(b) vector (Novagen, Germany), which was predigested with NcoI and BamHI, using a ligation kit (TaKaRa, Japan). Azu Cys F and Azu Cys R primers were designed to contain a mutant site for site-directed mutagenesis (SDM) and used to change the codon for Lys92Cys (K92C) from MG to TGC. Mutations in the azu gene were introduced using the SDM.

Expression and Purification of Recombinant Azurin Variants

The plasmids, containing genes for azurins, were transformed into E. coli BL21 (DE3). The transformants were grown to an OD of 0.6 at 37° C. in shake flasks containing 1 L of LuriaeBertani medium (0.5% yeast extract, 1.0% tryptophan, and 1.0% NaCl) with 50 mg/mL ampicillin. Expression was induced by adding isopropyl b-D-thiogalactopyranoside (IPTG) to a final concentration of 0.839 mM. The transformed cells were grown for an additional 16 hrs at 37° C. The cells were harvested by centrifugation at 5000 g for 15 min at 4° C. The cell paste was resuspended in sucrose buffer (20% sucrose, 0.3 M Tris-HCl, pH 8.1, 1 mM EDTA) and subjected to osmotic shock (0.5 mM $MgCl_2$). Contaminating proteins were precipitated from the periplasmic preparation by decreasing the pH to 3.8 (50 mM sodium acetate), yielding azurin-containing supernatant. Apo-azurin and cysteine-modified apo-azurin fractions (Elution pH 4.6 and 4.8, respectively) were separated on a CM excellulose ion-exchange column with a pH gradient from 4.0 to 6.0 (50 mM sodium acetate).

Preparation of Recombinant Azurin/GNP (Gold Nanopartides) Heterolayer

For sample preparation, Au substrates were cleaned using a piranha solution (30 vol % $H_2O_2$ and 70 vol % $H_2SO_4$) at 65° C. for 5 min to remove dust and organic residues on the surface of the substrates. The substrates were then cleaned with ethanol and deionized water repeatedly, and dried by $N_2$ gas. 20 mL of a prepared 0.1 mg/mL cysteine-modified azurin solution was placed onto the Au surface for direct immobilization on the Au surface through cysteine residues for 6 hrs. To prepare the recombinant azurin/GNP heterolayers, the recombinant azurin immobilized Au substrate was immersed in a 0.1 mM solution of 1-Octadecanethiol for 6 hrs. 20 mL of a 0.1 mg/mL of gold nanoparticle solution (20 mL) was then dipped into the recombinant azurin self-assembled substrate for 6 hrs. This process was conducted in a humidity chamber at 25° C. [19,25,26].

Surface Topographies of Azurin and Azurin/Gold Nanoparticle

The surface topographies of azurin and azurin/gold nanoparticle were investigated by AFM (Digital instruments Nanoscope (R) IV, USA). AFM was operated in tapping mode using a Phosphorous (n-type doped Si) tip (a spring constant: 20.80 N/m, a resonant frequency range: 230 to 305 kHz). A scan rate of 2.0 Hz was used during imaging. All images were acquired at a scan size of 400 nm×400 nm.

SPR (Multiskop™, Germany) was equipped with a He—Ne laser (632.8 nm) beam for investigating the biofilm formation. A glass prism (BK7, n=1.5168) was coated onto the Au surface and was the interfaced with oil as a matching solution between the prism and Au surface to reduce the air and bubble between the Au and prism. A Kretchmann's ATR coupler was used for the SPR spectroscopy. The reflected beam intensity was monitored using a photo multiplier tube (PMT) detector. Using this set up, the effects of total internal reflection could be reliably controlled. The operating angle shift was varied from 38" to 50".

Electrochemical Experiments of Recombinant Azurin and Azurin/GNP Heterolayer

This system was a conventional 3 electrodes system that consisted of a working electrode, counter electrode and reference electrode. The fabricated chip was used bought from BAS (USA) respectively. The electrochemical experiments were carried out with a CHI660A electrochemical workstation (CH Instruments, USA). All electrochemical experiments were carried out in the HEPES buffer solution.

2. Results

Redox Current of Recombinant Azurin/GNP Heterolayer

FIG. 1a shows a schematic of the basic electron transfer mechanism between recombinant azurin/gold nanoparticle heterolayers and the Au surface and FIG. 1b described the cyclic voltammogram of recombinant azurin and the recombinant azurin/GNP (GNP: 5 nm) heterolayer. The redox currents of the recombinant azurin/GNP heterolayers was shown to be 5 times higher than the recombinant azurin monolayer [5], which indicates the redox currents of recombinant azurin/gold nanoparticle were significantly higher when compared to recombinant azurin self-assembled on Au substrate.

In this invention, the redox properties of 5 different recombinant azurin/gold nanoparticle heterolayers (5 nm, 10 nm, 20 nm, 40 nm and 60 nm) were measured. The purpose of these experiments was to examine the electrochemical properties of each recombinant azurin/gold nanoparticle. The goal of these experiments was to assess their reduction potential and oxidation potential and determine if they were capable of performing memory functions with signal-enhanced currents. In this regard, we initially measured the cyclic voltammetry (CV) of each immobilized recombinant azurin/gold nanoparticle heterolayers. The results are shown in FIG. 3. We investigated the redox potential of all recombinant azurin/gold nanoparticle heterolayer samples. The oxidation potential and reduction potential of the recombinant azurin/GNP (5 nm) were 432.11 mV and 263.74 mV. The oxidation and reduction potential of recombinant azurin/GNP (10 nm) were 470.15 mV and 264.77 mV. In the case of recombinant azurin/GNP (20 nm), the oxidation and reduction potentials were 472.22 mV and 351.06 mV. The oxidation and reduction potentials of recombinant azurin/GNP (40 nm) were 457.89 mV and 358.91 mV. Finally, the oxidation potential and reduction potentials of recombinant azurin/GNP (60 nm) were 442.17 mV and 288.53 mV, respectively. These results are shown in FIGS. 2a-e.

Redox Current for Various Size of a Gold Nanopartide

Figure 2:
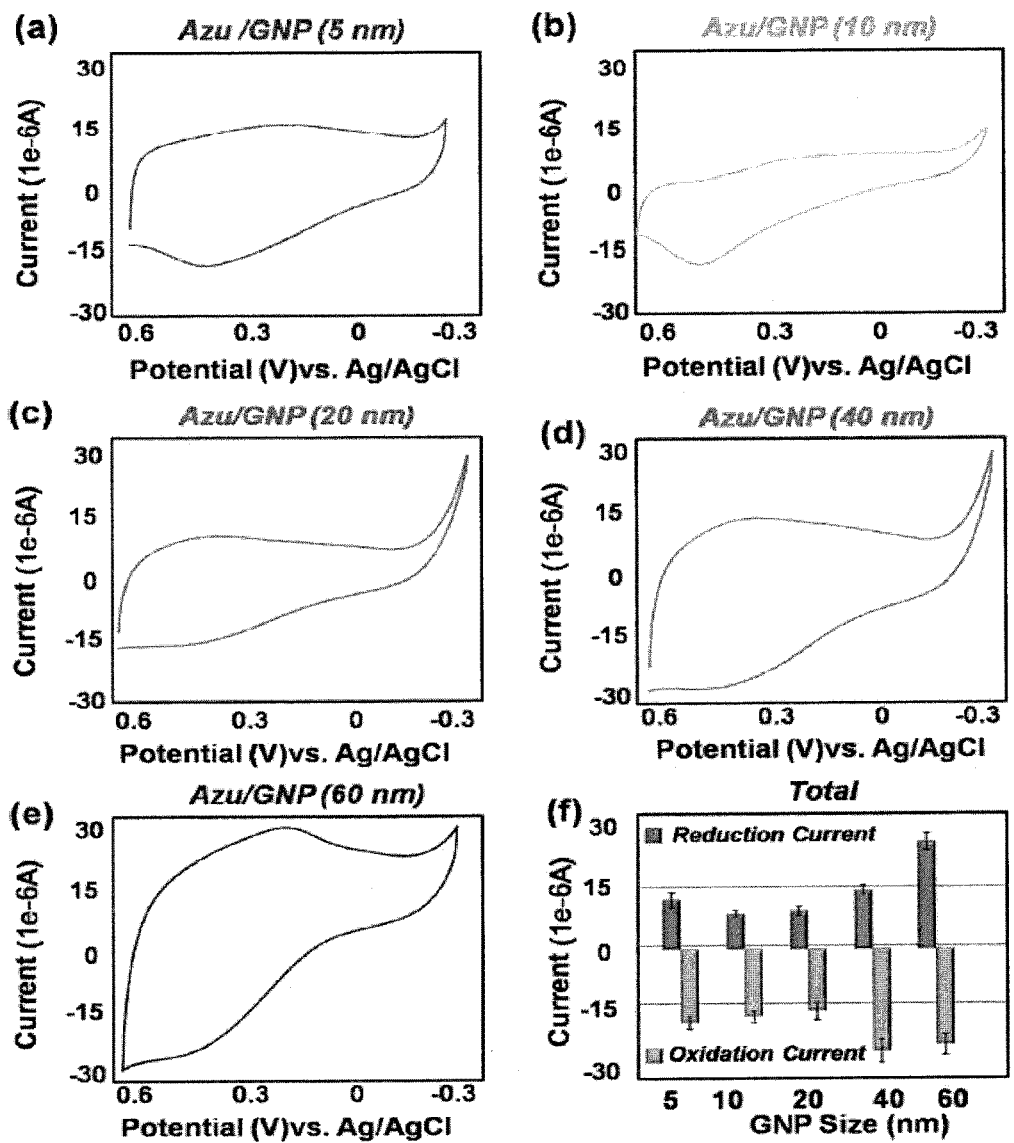
FIG. 2 shows the oxidation and reduction potentials of the various recombinant azurin/Au nanoparticle.
Figure 3:
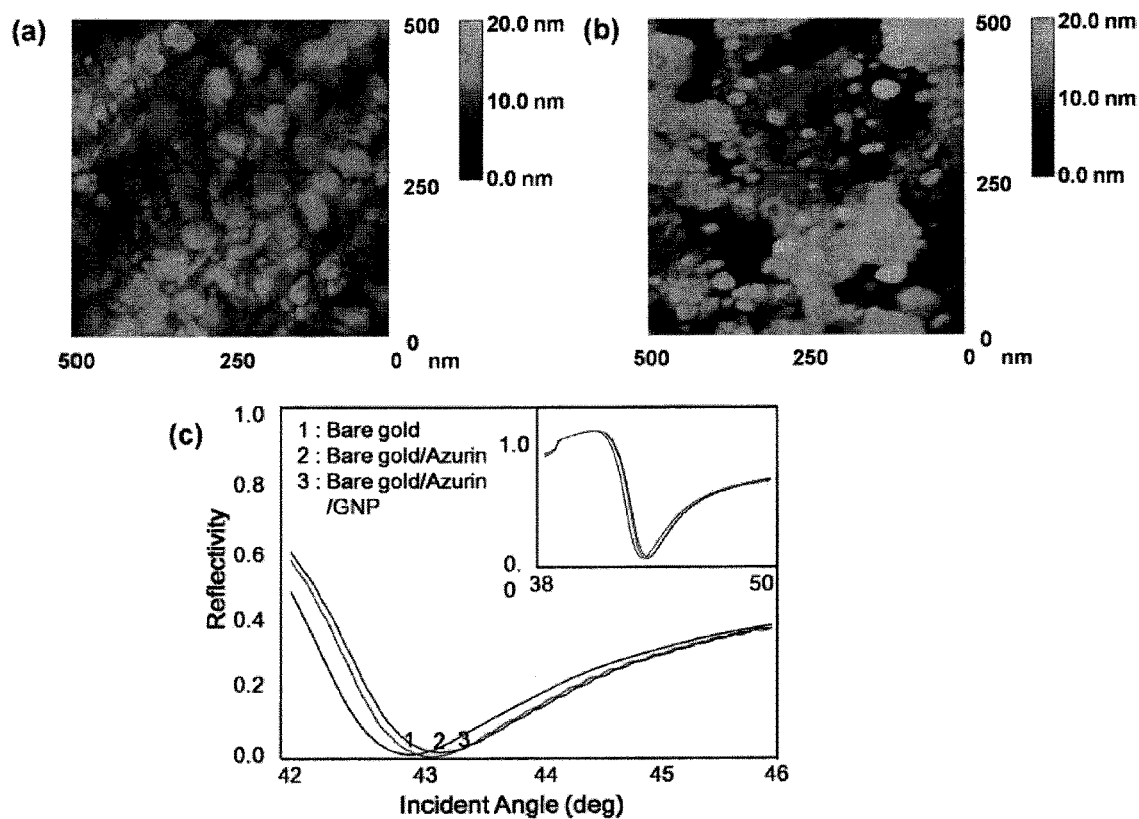
FIG. 3 shows a data on the cyclic voltammetry of the recombinant azurin/gold nanoparticle heterolayer.

The oxidation and reduction currents of various recombinant azurin/GNP heterolayers (5 nm, 10 nm, 20 nm, 40 nm and 60 nm) are described the FIG. 2f. The bars in the upper half indicated the reduction current and the bars in the lower half indicated the oxidation current. The oxidation current and reduction current of the recombinant azurin/GNP (5 nm) was $13.40\pm2.09$ µA and the oxidation potential was $-19.82\pm1.56$ µA. The reduction potential of the Azu/GNP (10 nm) layer was $9.61\pm0.72$ µA and the oxidation current was $-16.24\pm1.62$ µA. The reduction and oxidation currents of the Azu/GNP (20 nm) were $10.43\pm1.16$ µA and $-16.71\pm2.27$ µA. The oxidation and reduction currents of Azu/GNP (40 nm) were $15.98\pm1.13$ µA and $-27.4\pm3.14$ µA. Finally, for Azu/GNP (60 nm), the reduction and oxidation currents were $28.8\pm2.31$ µA and $-25.7\pm2.78$ µA.

Presumably, the difference in the redox currents was due to the size of the GNPs. In the case of Azu/GNP (5 nm), only one recombinant azurin was bound to the GNP since recombinant azurin is about 4.5 nm in size. However, when the size of GNP was increased to 10 nm, the redox currents decreased when compared to 5 nm GNP. This phenomenon was due to a hindrance of electron transfer between azurin and GNP. But, when the size of GNP was drastically increased up to 60 nm, the redox current increased. However, these redox currents originated from GNP directly. For this reason, the optimal GNP size was determined to be 5 nm.

Surface Topographies of Azurin and Azurin/Gold Nanopartide

The fabricated recombinant azurin/gold nanoparticle surface was then scanned by AFM to investigate the immobilization of the recombinant azurin/gold nanoparticle (GNP: 5 nm) heterolayers on the Au substrate, which was used as the working electrode. FIG. 3a shows the surface topography of the immobilized recombinant azurin layer, which contained irregular shaped lumps that were 20-30 nm. FIG. 3b depicts the adsorption of gold nanoparticles; this figure also shows that spherical particles formed on recombinant azurin-immobilized surface, where the molecular size of the clusters ranged from 10 to 15 nm. This variation in topography demonstrates that there is significant binding of gold nanoparticle/recombinant azurin to the Au substrate. SPR has been frequently utilized to observe and measure the immobilization of protein molecules on the surface of fabricated films. Thus, the plasmon resonance properties of the developed surface were observed to monitor interactions between recombinant azurin and the gold nanoparticles. A comparison between the angle shift for recombinant azurin on Au substrate and gold nanoparticle self-assembled on recombinant azurin modified Au surface is shown in FIG. 3c. An angle shift ($43.011\pm0.021$ to $43.172\pm0.034$) was observed after recombinant azurin self-assembled onto the Au surface. In addition, there was a significant angle shift from $43.011\pm0.021$ to $43.254\pm0.048$ after the gold nanoparticle was immobilized onto the recombinant azurin modified Au surface. This result indicates that gold nanoparticles successfully self-assembled onto the Au surface via recombinant azurin. The angle shift due to immobilization of recombinant azurin on to Au surface and the gold nanoparticle self-assembled onto the azurin-modified Au surface was 0.172 and 0.254, respectively. Thus, SPR and AFM both verified that recombinant azurin/gold nanoparticles were successfully self-assembled and well-oriented on the Au substrates.

Examination of a Signal-Enhanced Memory

The chronoamperometry (CA) method was used to assess the signal-enhanced memory performance of this device. The CA is an electrochemical method where the working electrodes potential is applied, repeatedly and the faradaic current from the applied potential at the working electrode is observed as a function of time. Using this approach, the oxidation potential (OP) and reduction potential (RP), which were obtained from the previous CV experiments, were applied to recombinant azurin. The OP step can be regarded as the Write function, which transfers the charge from the external substrate to the recombinant azurin. The introduction of the RP causes the charge to be transfer from the recombinant azurin molecules. Thus, using this system, a 2-state biomemory was established. To allow more charge to be stored into the defined area, gold nanoparticles were introduced to the recombinant azurin immobilized Au substrate. When an OP of 432.11 mV and RP of 236.74 mV were applied to the recombinant azurin/gold nanoparticle electrode repeatedly, the amplified-faradaic current was monitored and compared to the recombinant azurin-immobilized working electrode. The current signal change from an application of OP and RP can be used as an information value of '1' and '0'.

Figure 4:
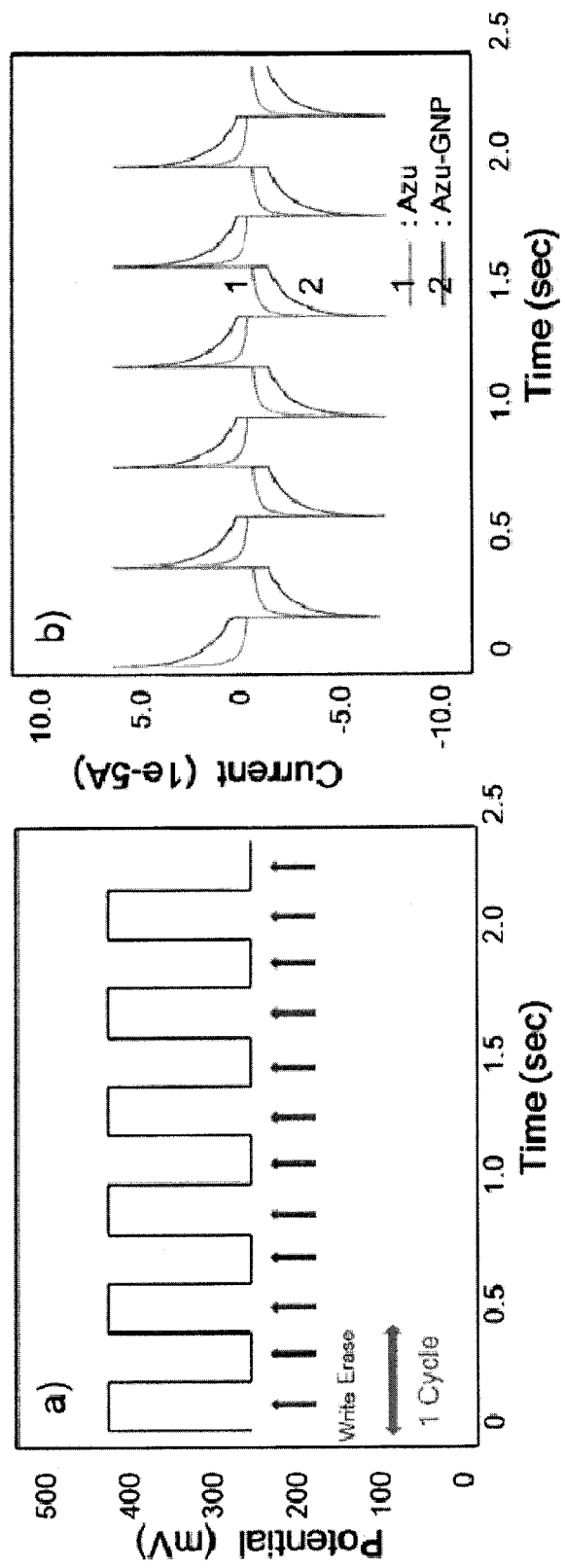
FIG. 4 shows a signal enhanced 2-state memory function of the biomemory based on the recombinant azurin/gold nanoparticle heterolayer by chronoamperometry.

FIG. 4a shows a diagram of the applied potentials. FIG. 4b shows that the current inflow and outflow from the fabricated electrode were stable when an oxidation potential (432.11 mV) and reduction potential (236.74 mV) were applied repeatedly. In the case of the recombinant azurin immobilized electrode, the corresponding current response displayed a 2-state memory behavior, which is demonstrated in Curve 1 of FIG. 4b. However, for the recombinant azurin/gold nanoparticle immobilized electrode, the corresponding current signals were drastically higher, which is shown in Curve 2 of FIG. 4b, when compared to the recombinant azurin immobilized electrode. Using these currents values, the stored charge of the recombinant azurin layer and recombinant azurin/gold nanoparticle heterolayers were calculated from the following equation.

$$Q = \int i dt$$

The amount of charge stored in the recombinant azurin and recombinant azurin/gold nanoparticle by writing or erasing was obtained from the currents shown in the CA. The charged currents of the recombinant azurin monolayer and recombinant azurin/gold nanoparticle heterolayers were calculated to be approximately ≈1.1413 μC and ≈4.503 μC, respectively. This result demonstrated the recombinant azurin/gold nanoparticle heterolayers stored more charge when compared to the recombinant azurin layer. The charged electrons of 3.3617 μC originated from the interaction between recombinant azurin and gold nanoparticle. These results clearly demonstrate that the gold nanoparticles could significantly enhance the signal element in a biomemory device.

In the present invention, a signal-enhanced biomemory device was developed to store more charge in a defined area. For this purpose, a cysteine-modified azurin/gold nanoparticle heterolayer was fabricated onto an Au substrate. Based on the AFM and SPR results, the recombinant azurin/gold nanoparticle heterolayers were successfully fabricated and well oriented. The CV results demonstrated that various recombinant azurin/gold nanoparticle heterolayers had amplified redox currents when compared to the recombinant azurin monolayer. The signal-enhanced biomemory function was verified using chronoamperometry (CA) under the same conditions. As a result, the basic concept of a signal-enhanced biomemory device was established. Thus, in this invention, a new type and material combination for the development of a biomolecular memory system was established. In addition, this biomemory device holds promise as an effective alternative to silicon-based memory devices and can be used to perform memory function at the nanoscale.

REFERENCES

[1] P. N. Bartlett in Bioelectrochemistry: Fundamentals, Experimental Techniques and Applications, 1st ed., Wiley, Chichester, West Sussex, UK 2008, pp. 3-38.
[2] D. E. Woolley, L. C. Tetiow, D. J. Adlam, D. Gearey, R. D. Eden, T. H. Ward, T. D. Allen, Exp. Cell. Res. 2002, 273, 65.
[3] H. N. Li, Y. X. Ci, J. Feng, K. Cheng, S. Fu, D. B. Wang, Bioelectrochem. Bioenerg. 1999, 48, 171.
[4] C. Xiao, B. Lachance, G. Sunahara, J. H. T. Luong, Anal. Chem. 2002, 74, 5748.
[5] C. Xiao, J. H. T. Luong, Biotechnol. Prog. 2003, 19, 1000.
[6] S. Arndt, J. Seebach, K. Psathaki, H. J. Galla, J. Wegener, Biosens. Bioelectron. 2004, 19, 583.
[7] K. Kerman, M. Kobayashi, E. Tamiya, Measure. Sci. Tech. 2004, 15, R1.
[8] J. Wang, Biosens. Bioelectron. 2006, 21, 1887.
[9] K. Kerman, M. Vestergaard, N. Nagatani, Y. Takamura, E. Tamiya, Anal. Chem. 2006, 8, 2182.
[10] A. Bini, M. Minunni, S. Tombelli, S. Centi, M. Mascini, Anal. Chem. 2007, 79, 3016.
[11] J. Newman, A. P. F. Turner, Biosens. Bioelectron. 2005, 20, 2435.
[12] K. Kerman M. Vestergaard, E. Tamiya, "Methods in Biotechnology" in Electrochemical Biosensors (Ed: A. Rasooly), Humana Press, USA, in press.
[13] S. Centi, S. Tombelli, M. Minnuni, M. Mascini, Anal. Chem. 2007, 79, 466.
[14] F. A. Armstrong, in Bioelectrochemistry (Ed: G. S. Wilson), Wiley-VCH, Weinheim 2002, pp. 11. 29.
[15] J.-W. Choi, B.-K. Oh, J. Min, Y. J. Kim, Appl. Phys. Lett. 2007, 91, 263902.
[16] T. Lee, S.-U. Kim, J. Min, J.-W. Choi, Adv. Mater. 2010, 22, 510.
[17] T. Lee, J. Min, S.-U. Kim, J.-W. Choi, Biomaterials 2011, 32, 3815.
[18] T. Lee, W. A. El-Said, J. Min, J.-W. Choi, Biosens. Bioelectron. 2011, 26, 304.
[19] S.-U. Kim, A. K. Yagati, J. Min, J.-W. Choi, Biomaterials 2010, 31, 1293.
[20] M. Aubin-Tam, K. Hamad-Schifferli, Biomed. Mater. 2008, 034001.
[21] P. S. Jensen, Q. Chi, J. Zhang, J. Ulstrup, J. Phys. Chem. C 2009, 113, 13993.
[22] J. Min, T. Lee, S.-M. Oh, H. Kim, J.-W. Choi, Bioetchnol. Bioprocess Eng. 2010, 15, 30.
[23] P. S. Jensen, Q. Chi, F. B. Grumsen, J. M. Abad, A. Horsewell, D. J. chiffrin, J. Ulstrup, J. Phys. Chem. C 2007, 111, 6124.
[24] M. Bixon, B. Giese, S. Wessely, T. Langenbacher, M. E. Michel-eyerle, J. Jortner, Proc. Natl. Acad. Sci. USA 1999, 96, 11713.
[25] J. Min, S.-U. Kim, C.-H. Yea, J.-W. Choi, J. Nanosci. Nanotechnol. 2008, 8, 4982.
[26] T. Lee, S.-U. Kim, J.-H. Leed. Mind.-W. Choi, J. Nanosci. Nanotechnol. 2009, 9, 7136.

What is claimed is:

1. A biomemory device, comprising
   (a) a substrate; and
   (b) a heterolayer comprising azurin and a gold particle with a size of 1-10 nm;
   wherein the heterolayer is immobilized on the substrate, and
   wherein the azurin is directly immobilized on the substrate via a cysteine residue introduced to the azurin.

2. The biomemory device according to claim 1, wherein the substrate is a metal, metal oxide, glass, ceramic, quartz, silicon, semiconductor, $Si/SiO_2$ wafer, germanium, gallium arsenide, carbon, carbon nanotube, polymer, sepharose or agarose substrate.

3. The biomemory device according to claim 1, wherein the substrate is a gold (Au) substrate.

4. The biomemory device according to claim 1, wherein the biomemory device is operated by applying a reduction potential and an oxidation potential to the biomemory device.

* * * * *